United States Patent [19]

Bollens et al.

[11] Patent Number: 5,705,148
[45] Date of Patent: Jan. 6, 1998

[54] USE OF HYDRO- AND FLUOROCARBON COMPOUNDS IN COSMETIC COMPOSITIONS; HYDRO- AND FLUOROCARBON COMPOUNDS; AND COSMETIC COMPOSITIONS CONTAINING THESE COMPOUNDS

[75] Inventors: Eric Bollens, Saint-Maurice; Claude Mahieu, Paris, both of France

[73] Assignee: L'Oreal, Paris, France

[21] Appl. No.: 379,529

[22] PCT Filed: Jun. 1, 1994

[86] PCT No.: PCT/FR94/00634

§ 371 Date: Mar. 21, 1995

§ 102(e) Date: Mar. 21, 1995

[87] PCT Pub. No.: WO94/27944

PCT Pub. Date: Dec. 8, 1994

[30] Foreign Application Priority Data

Jun. 2, 1993 [FR] France ................ 93 06605

[51] Int. Cl.⁶ .................. A61K 7/00; A61K 7/07
[52] U.S. Cl. .............. 424/70.1; 424/401; 514/743; 514/749
[58] Field of Search ............... 424/70.1, 401, 424/70.22; 514/743, 759

[56] References Cited

U.S. PATENT DOCUMENTS 4,113,748 9/1978 Hager et al. .............. 260/348.43

FOREIGN PATENT DOCUMENTS

| 0 240 601 | 10/1987 | European Pat. Off. |
| 0 457 688 | 11/1991 | European Pat. Off. |
| 0 498 716 | 8/1992 | European Pat. Off. |
| WO 93/11103 | 6/1993 | WIPO |

OTHER PUBLICATIONS

Database WPI, Week 8937, Derwent Publications Ltd.
Patent Abstracts of Japan, vol. 17, No. 067 JP4275248.

*Primary Examiner*—Sally Gardner-Lane
*Attorney, Agent, or Firm*—Jacobson, Price, Holman & Stern, PLLC

[57] ABSTRACT

The present invention concerns the use of hydrofluorocarbon compounds with formula (I):

$$R_F\text{-}(CH_2)_n\text{-}X\text{-}[C_3H_5(OH)]\text{-}Y\text{-}(CH_2)_m\text{-}R'_F \qquad (I')$$

where
$C_3H_5(OH)$ represents the structures:

$$-CH_2-\underset{\underset{OH}{|}}{CH}-CH_2- \qquad (Ia)$$

or $$-\underset{\underset{CH_2OH}{|}}{CH}-CH_2- \qquad (Ib)$$

or $$-CH_2-\underset{\underset{CH_2OH}{|}}{CH}- \qquad (Ic)$$

$R_F$ and $R_{F'}$, which may be identical or different, represent a perfluorinated linear or branched $C_4$–$C_{20}$ alkyl radical or a mixture of perfluorinated linear or branched $C_4$–$C_{20}$ alkyl radicals;

m and n, which may be identical or different, are 0, 1, 2, 3 or 4;

X and Y, which may be identical or different, represent O or S. It also concerns certain of these compounds and cosmetic compositions containing these compounds.

7 Claims, No Drawings

USE OF HYDRO- AND FLUOROCARBON COMPOUNDS IN COSMETIC COMPOSITIONS; HYDRO- AND FLUOROCARBON COMPOUNDS; AND COSMETIC COMPOSITIONS CONTAINING THESE COMPOUNDS

This application has a filing date of Jun. 1, 1994 under 35 USC 371 and a filing date of Jun. 2, 1993 under 35 USC 119.

The present invention concerns the use of hydro- and fluorocarbon compounds in cosmetic compositions, cosmetic compositions containing these compounds and certain novel compounds.

Perfluoropolyethers are known for their use in cleaning, protecting or making up the skin, or for washing hair. These compounds are known to have a low surface tension and are easy to spread, but have very low solubility in most fluids apart from fluorine-containing fluids. This means that they are very difficult to incorporate into cosmetic composition formulations. Some of these compounds, perfluoromethylisopropylethers, are sold by MONTEFLUO under the trade name "FOMBLIN HC".

We have now discovered compounds which have improved solubilities over FOMBLIN compounds in certain of the solvents which are normally used in cosmetics. Their properties mean that they are readily dispersible in certain cosmetic media and render the compositions of which they form a part very stable.

The present invention thus concerns the use of compounds with formula:

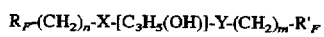    (I)

where
$C_3H_5(OH)$ represents the structures:

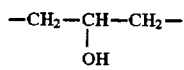    (Ia)

or

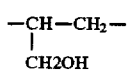    (Ib)

or

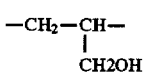    (Ic)

$R_F$ and $R_{F'}$, which may be identical or different, represent a perfluorinated linear or branched $C_4$–$C_{20}$ alkyl radical or a mixture of perfluorinated linear or branched $C_4$–$C_{20}$ alkyl radicals;

m and n, which may be identical or different, are 0, 1, 2, 3 or 4;

X and Y, which may be identical or different, represent O or S.

Preferred compounds are those in which $R_F$ and $R_{F'}$ represent a perfluorinated linear or branched $C_6$–$C_{10}$ radical, X and Y are not both O, n and m equal 2 and —$C_3H_5(OH)$— is linear.

Of the compounds with formula (I), the following compounds with formula (I') are novel:

    (I')

where
$C_3H_5(OH)$ represents the structures:

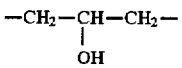    (Ia)

or

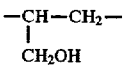    (Ib)

or

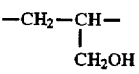    (Ic)

$R_F$ and $R_{F'}$, which may be identical or different, represent a perfluorinated linear or branched $C_4$–$C_{20}$ alkyl radical or a mixture of perfluorinated linear or branched $C_4$–$C_{20}$ alkyl radicals;

m and n, which may be identical or different, are 0, 1, 2, 3 or 4, and X represents O and Y represents S or X represents S and Y represents O.

Preferred compounds with formula (I') are those in which $R_F$ and $R_{F'}$ represent a linear or branched $C_6$–$C_{10}$ perfluorinated radical, n and m equal 2, and $C_3H_5(OH)$ represents structure (Ia).

Compounds with formula (I) in accordance with the invention can be prepared by reacting a fluorine-containing compound containing an acidic hydrogen with formula (II):

    (II)

with an epoxide with formula (III):

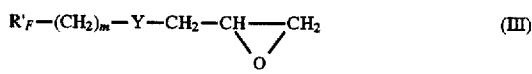    (III)

or by reacting a fluorine-containing compound containing an acidic hydrogen with formula (IV):

    (IV)

with a fluorine-containing epoxide with formula (V):

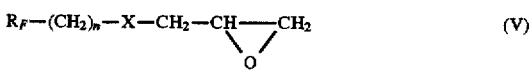    (V)

in the presence of an acidic or basic compound which acts as a reactant or as a catalyst, to produce the corresponding compound with formula (I). Substituents RF, RH, n and x have the same meanings in formulae (II), (III), (IV) and (V) as those given for formula (I), and X and Y represent O or S.

Compounds with formula (V) are described in U.S. Pat. No. 3,976,698, in European patent application EP-A-0 300 358 and in German patent application DE-A-2 018 461.

When X represents S in formula (II) or (IV), a basic compound is preferably used.

The compounds which act as a reactant or as a catalyst may thus be basic, such as alkali metals, alkali or alkaline earth metal hydroxides, alkali metal alcoholates such as methylates or tertiobutylates, alkaline hydrides such as sodium hydride, or tertiary amines such as pyridine or triethylamine. They may also be Lewis bases, for example cesium, rubidium or potassium fluoride. These compounds may be supported on a solid support such as alumina.

Preferably, an alkali alcoholate such as sodium methylate or a tertiary amine such as pyridine is used.

These compounds may also be acids, in particular when the starting material with formula (II) or (IV) is an alcohol. These acids may be inorganic acids or their tertiary amine salts, or Lewis acids such as boron trifluoride, tin tetrachloride, or antimony pentachloride, used neat, in solution or associated with any normal support.

The concentration of acidic or basic compounds acting as reactant or catalyst and used in preparing compounds with formula (I) can be between 1% and 100% molar, preferably between 2% and 10% molar with respect to the fluorine-containing compound with an acidic hydrogen with formula (II) or (IV).

The preparation can be carried out in the presence or absence of a solvent.

Examples of solvents are aliphatic hydrocarbons such as heptane or hexane, cyclic hydrocarbons such as cyclohexane, aromatic hydrocarbons such as toluene, ethers such as ethyl ether, isopropyl ether or tert-butyl ether, cyclic ethers such as dioxane, or acetonitrile, dimethylformamide, N-methylpyrrolidone, or dimethylacetamide.

When the compound with formula (II) or (IV) is a thiol (X=S), alcohols such as methanol, ethanol or isopropanol can also be used as a solvent.

The compounds with formula (I) can be prepared by firstly mixing the compound containing an acidic hydrogen with formula (II) or (IV) with the acidic or basic reactant or catalyst in an inert atmosphere. Mixing can be carried out at a temperature of between 20° C. and 180° C., preferably between 50° C. and 150° C. The term "inert atmosphere" means an atmosphere of nitrogen, argon or helium, for example.

Mixing can be effected in the presence or absence of a solvent, depending on the nature of the compound containing the acidic hydrogen and the reactant or catalyst.

The epoxide with formula (III) or (V) is then added to the mixture obtained. Addition can be effected all at once or gradually, over a period of 30 minutes to 2 hours, for example.

The reaction time is thus between about 1 hour and 24 hours, preferably between 1 hour and 3 hours.

When it contains a mercaptan function, the compound produced by the reaction can be oxidized to a sulfoxide or sulfone in the presence of hydrogen peroxide in an acidic medium, using known methods, particularly as described in French patents FR-A-2 099 092 and FR-A-2 516 920.

It may also be necessary to neutralize the mixture obtained and separate the synthesized compound using conventional methods, for example distillation.

When a compound with formula (I) is prepared in the presence of a basic compound it produces only compounds in which $C_3H_5(OH)$ represents group (Ia). When the reaction is carried out in the presence of an acidic compound a mixture of compounds can be obtained corresponding to designations (Ia), (Ib) and (Ic) of $C_3H_5(OH)$.

The compound of the invention can be in the form of an oil, or it may be solid at room temperature.

Compounds with formula (I) where X and Y are identical are known, in particular from German patent application DE-A-2 702 607, Japanese patent applications JP-89 193 236 and JP-92 275 248, and United States patent U.S. Pat. No. 3,893,984.

In general, these compounds are used in cosmetic compositions to improve the cosmetic properties. They provide smoothness, gloss and a non-sticky feel to keratinous material such as skin, hair and nails. In addition, some of these compounds are in the form of a colorless oil and can thus be used to produce transparent emulsions.

The invention thus also concerns a cosmetic composition characterized in that it contains at least one compound with formula (I) as defined above and at least one cosmetic additive.

The composition can be in the form of an emulsion, milk or cream, oily or oleoalcoholic lotion, oily or oleoalcoholic gel, ionic or non-ionic amphiphilic lipid based vesicular dispersion, solid stick, paste, spray or aerosol foam.

Depending on the form of the composition into which the compound of the invention is incorporated, the compositions also contain additives which are normal for the selected form.

More precisely, the composition can be a milk or cream for skin or hair, a make-up removing cream, lotion or milk, a sun protection cream, gel, milk or lotion, a shaving cream or foam, an aftershave lotion, a shampoo or conditioner, a styling gel, a direct hair dye, a hair perming lotion, a body deodorant, a toothpaste, a lacquer, a lip care product or a nail care product.

The cosmetic composition can also be used as make-up for eyelashes, eyebrows, nails, lips or for skin in epidermal treatment creams, a foundation, lipstick, eye-shadow, blusher, eyeliner, mascara or nail polish, for example.

In accordance with the invention, compounds with formula (I) represent 0.1% to 25%, preferably 0.1% to 15% of the total composition weight.

Examples of normal cosmetic additives which can also be present in this type of composition are the usual fatty substances, organic solvents, silicones, thickeners, softeners, UV-A or UV-B or broad spectrum solar filters, anti-foaming agents, moisturising agents, humectants, fragrances, preservatives, surfactants, fillers, sequestrating agents, emulsifiers, anionic, cationic, non-ionic or amphoteric polymers and their mixtures, antiperspirants, alkalinizing agents, dyes, pigments, propellants, reducing agents, anti-oxidizing agents and free radical absorbers.

More precisely, examples of fatty substances are oils or waxes or their mixtures, fatty acids, fatty alcohols, fatty acid esters such as $C_6$ to $C_{18}$ fatty acid triglycerides, vaseline, paraffin, lanolin, or hydrogenated or acetylated lanolin.

Examples of oils are mineral, animal, vegetable or synthetic oils, in particular vaseline oil, paraffin oil, castor oil, jojoba oil, sesame seed oil, and silicone and isoparaffin oils and gums.

Particular examples of animal, fossil, vegetable, mineral or synthetic waxes are beeswax, Carouba wax, Candelilla wax, ozokerites, microcrystalline waxes and silicone waxes and resins.

Examples of organic solvents which are generally used in cosmetic compositions are $C_1$ to $C_6$ low monoalcohols or polyalcohols such as ethanol, isopropanol, isopropyl alcohol, propyleneglycol, glycerol, sorbitol, ketones such as acetone, esters such as butyl acetate, ethyl acetate or isopropyl myristate, and toluene.

Examples of thickeners are cellulose derivatives, polyacrylic acid derivatives, guar gum or carouba gum and xanthane gum.

Examples of surfactants are non-ionic surfactants such as alkyl($C_8$–$C_{24}$)polyglycosides where the number of glucoside units is between 1 and 15 and non-ionic polyglycerolated surfactants.

Particular alkylpolyglycosides are those sold under the trade name APG, such as APG 300, APG 350, APG 500, APG 550, APG 625 and APG base 10-12; and products sold by SEPPIC under the trade names TRITON CG 110 and TRITON CG 312.

The polyglycerolated compounds are derivatives resulting from condensation of 1 to 10, preferably 2 to 6 moles of glycidol with one mole of $C_{10}$–$C_{14}$ alcohol or alphadiol, or $C_{12}$–$C_{18}$ fatty acid diglycolamides, such as those described in French patents FR-A-1 477 048, FR-A-2 328 763, FR-A-2 091 516 and FR-A-2 169 787.

The vesicular dispersions of ionic or non-ionic amphiphilic lipids mentioned above can be prepared using normal techniques, for example as described in "Les liposomes en biologie cellulaire et pharmacologie", Ed. INSERM/John Libbery Eurotext (1987), pp 6–18.

For toothpaste compositions, the usual additives can be used such as polishing agents for example silica, active ingredients such as fluorides, for example sodium fluoride, and optional sweetening agents, for example sodium saccharinate.

The following examples illustrate the invention and do not in any way limit its scope.

PREPARATION EXAMPLES

EXAMPLE I 1-(2'-F-hexylethylthio)-3-(2'-F-hexylethoxy)-2-propanol 1.33 g of a methanolic solution of sodium methylate (about 30% - 5.65 meq g-1) was added to 57 g of 2-F-hexylethanethiol at a temperature of 25° C., with stirring and in a stream of nitrogen, over a period of one minute.

The mixture was heated to 70° C. The methanol present in the mixture was evaporated off under vacuum.

The 2-F-hexylethylglycidylether (63 g - 0.15 mole) was added dropwise over one hour. The temperature of the mixture was maintained at 60° C. to 70° C. during addition of the epoxide.

After addition, the temperature was reduced to 25° C.

The mixture was neutralized using 7.5 ml of normal HCl. 1-(2'-F-hexylethylthio)-3-(2'-F-hexylethoxy)-2-propanol was separated by distillation: B Pt=170° C./133 Pa.

85 g (71%) of a colorless translucent oil was obtained. Elemental analysis:

|  | % C | % H | % S | % F |
| --- | --- | --- | --- | --- |
| Calculated | 28.51 | 1.76 | 4.01 | 61.72 |
| Measured | 28.60 | 1.79 | 4.32 | 61.54 |

EXAMPLE II 1,3-bis-(2'-F-hexylethylthio)-2-propanol 14.7 g of powdered anhydrous sodium methylate was introduced into a one liter triple necked flask and covered with 300 ml of anhydrous methanol. The methylate dissolved in the methanol in a nitrogen atmosphere over 10 minutes at room temperature.

99.75 g of 2-F-hexylethanethiol (0.2625 mole) was added at room temperature over 10 minutes; then with the mixture cooled to 5° C. in an ice bath, a solution of 15 g of 1,3-dichloro-2-propanol (0.131 mole) in 75 ml of methanol was added.

When addition was complete the ice bath was removed and the mixture was allowed to return to room temperature. It was then heated for 1 hour at 40° C.

The mixture was hydrolyzed with 500 ml of water and the product was extracted with isopropyl ether. The organic phase was dried over sodium sulfate and filtered through filter paper and the solvent was evaporated off under reduced pressure.

A very pale oil was obtained which solidified on cooling.

The product was taken up in 400 ml of refined petroleum spirit and then filtered and dried on filter paper.

65 g (62%) of 1,3-bis-(2'-F-hexylethylthio)-2-propanol was obtained as a white solid with a melting point of 49° C. Elemental analysis:

|  | % C | % H | % S | % F |
| --- | --- | --- | --- | --- |
| Calculated | 27.95 | 1.73 | 7.85 | 60.51 |
| Measured | 27.85 | 1.63 | 7.81 | 60.38 |

EXAMPLE III 1,3-bis-(2'-F-octylethylthio)-2-propanol 14.7 g of powdered anhydrous sodium methylate was introduced into a one litre triple necked flask and covered with 300 ml of anhydrous methanol. The methylate dissolved in the methanol in a nitrogen atmosphere over 10 minutes at room temperature.

125 g of 2-F-octylethanethiol (0.2625 mole) was added at 25° C. over 15 minutes; then with the mixture cooled to between 0° C. and 5° C., a solution of 15 g of 1,3-dichloro-2-propanol (0.131 mole) in 80 ml of methanol was added over 10 minutes.

The mixture was allowed to return to room temperature. It was then heated for 1 hour at 40° C.

The mixture was hydrolyzed with 500 ml of water and the product was extracted with 600 ml of isopropyl ether.

The organic phase was decanted, dried over sodium sulfate and filtered through filter paper and the solvent was evaporated off.

A solid was obtained which was taken up in 500 ml of refined petroleum spirit then filtered through n°4 sintered glass.

102 g (77%) of 1,3-bis-(2'-F-octylethylthio)-2-propanol was obtained as a white powder with a melting point of 91° C.

Elemental analysis:

|  | % C | % H | % S | % F |
| --- | --- | --- | --- | --- |
| Calculated | 27.18 | 1.39 | 6.31 | 63.55 |
| Measured | 27.22 | 1.47 | 6.25 | 63.87 |

FORMULATION EXAMPLES

EXAMPLE 1

| Oil-in-water solar protection emulsion | |
| --- | --- |
| Phase A | |
| Mixture of cetylstearyl alcohol and cetylstearyl alcohol oxyethylenated with 33 moles of ethylene oxide (80/20), sold by TENSIA under the trade name DEHSCONET 390 | 7 g |
| Glyceryl stearate sold by GATTEFOSSE under the trade name GELEOL COPEAUX | 2 g |
| Silicone oil sold by RHONE POULENC under the trade name SILBIONE HUILE 70 047 V 300 | 1.5 g |
| Cetyl alcohol | 1.5 g |
| Vaseline oil | 15 g |

-continued

| Oil-in-water solar protection emulsion | |
|---|---|
| Compound of Example (I) | 0.5 g |
| Glycerol | 20 g |
| Preservatives | qs |
| Phase B | |
| 2-ethylhexylparamethoxycinnamate, sold by GIVAUDAN under the trade name PARSOL MCX | 5 g |
| Sterilized demineralized water | qsp 100 g |

The emulsion was produced by adding oily phase A at about 80° C. to aqueous phase B at the same temperature, with rapid stirring. An oil-in-water emulsion was obtained in the form of a cream.

EXAMPLE 2

| Oil-in-water self-tanning emulsion | |
|---|---|
| Phase A | |
| Mixture of cetylstearyl alcohol and cetylstearyl alcohol oxyethylenated with 33 moles of ethylene oxide (80/20), sold by TENSIA under the trade name DEHSCONET 390 | 7 g |
| Glyceryl stearate sold by GATTEFOSSE under the trade name GELEOL COPEAUX | 2 g |
| Silicone oil sold by RHONE POULENC under the trade name SILBIONE HUILE 70 047 V 300 | 1.5 g |
| Cetyl alcohol | 1.5 g |
| Vaseline oil | 15 g |
| Compound of Example (II) | 0.3 g |
| Glycerol | 20 g |
| Preservatives | qs |
| Phase B | |
| Dihydroxyacetone | 3 g |
| Sterilized demineralized water | qsp 100 g |

The method used was identical to that of Example 1.

EXAMPLE 3

| Oil-in-water after-sun emulsion | |
|---|---|
| Phase A | |
| Mixture of cetylstearyl alcohol and cetylstearyl alcohol oxyethylenated with 33 moles of ethylene oxide (80/20), sold by TENSIA under the trade name DEHSCONET 390 | 7 g |
| Glyceryl stearate sold by GATTEFOSSE under the trade name GELEOL COPEAUX | 2 g |
| Silicone oil sold by RHONE POULENC under the trade name SILBIONE HUILE 70 047 V 300 | 1.5 g |
| Cetyl alcohol | 1.5 g |
| Vaseline oil | 15 g |
| Compound of Example (III) | 0.2 g |
| Glycerol | 20 g |
| Preservatives | qs |
| Phase B | |
| α-bisabolol | 0.5 g |
| Sterilized demineralized water | qsp 100 g |

The method used was identical to that of Example 1.

EXAMPLE 4

Skin cream—Oil-in-water emulsion

A skin cream was prepared in the form of an oil-in-water emulsion with the following composition:

| Phase A | |
|---|---|
| Non-ionic hydroxypropylether surfactant obtained by condensation, with alkaline catalysis, of 3.5 moles of glycidol with a mixture of $C_{11}$–$C_{14}$ alphadiols, in accordance with French patent FR-A-2 091 516 | 2.4 g |
| Methyl parahydroxybenzoate | 0.2 g |
| Glycerine | 5 g |
| Water | 22.06 g |
| Phase A' | |
| Gel of glyceryl polyacrylate in water (50/50), sold by HISPANO CHEMICA under the trade name HISPAGEL 100 | 56.14 g |
| Phase B | |
| Cetyl alcohol | 1 g |
| Compound of Example I | 5 g |
| Apricot kernel oil | 5 g |
| Sesame seed oil | 1.5 g |
| Caprylic/capric acid triglyceride, sold by HULS under the trade name MIGLYOL 812 | 1.5 g |
| Propyl parahydroxybenzoate | 0.2 g |

Method:

Phase A was heated to 80° C. Phase A' was added, with stirring, followed by phase B which had been heated to 80° C. The mixture was allowed to cool to room temperature, maintaining the stirring.

The compound of Example I could be replaced by the compound of Example II or Example III.

EXAMPLE 5

| Lipstick A lipstick was prepared with the following composition: | |
|---|---|
| Compound of Example I | 1 g |
| Ozokerite | 14.90 g |
| Microcrystalline wax | 4.90 g |
| Candelilla wax | 7.40 g |
| Jojoba oil | 6.20 g |
| Castor oil | 1.20 g |
| Liquid lanoline | 18.60 g |
| Acetylated lanoline | 9.90 g |
| Vaseline oil | 11.10 g |
| Talc | 3.70 g |
| Micatitanium | 8.70 g |
| D&C Red n° 7 Ca lake | 5.20 g |
| D&C Red n° 7 Ba lake | 2.80 g |
| FD&C Yellow n°5 | 1 g |
| Titanium dioxide | 3.10 g |
| Butylhydroxytoluene | 0.30 g |
| Fragrance | qs |

The oils were mixed at a temperature of 50° C. to 60° C. The pigments and organic lacquers were ground in the oily phase.

The molten waxes were then added, followed by the talc and the micatitanium, then the fragrance.

The composition was then poured into a mold.

The lipstick was easy to apply (slid on easily) and made the lips soft.

The compound of Example I could be replaced by the compound of Example II or Example III.

EXAMPLE 6

Nail polish
A nail polish was prepared with the following composition:

| | |
|---|---|
| Compound of Example I | 1 g |
| Nitrocellulose | 10.75 g |
| Toluene sulfonamide formaldehyde resin, sold by AKZO under the trade name KETJENFLEX MS80 | 9.70 g |
| Tributyl acetylnitrate sold by PFIZER under the trade name CITROFLEX A4 | 6.45 g |
| Toluene | 30.70 g |
| Butyl acetate | 21.50 g |
| Ethyl acetate | 9.20 g |
| Isopropyl alcohol | 7.70 g |
| Citric acid | 0.05 g |
| Stearalkonium hectorite | 1.45 g |
| Pigments | 1.50 g |

The polish was easy to apply to the nail to give a film which adhered well to the nail and had a high gloss. The gloss was retained for a long period.

EXAMPLE 7

Shampoo

| | |
|---|---|
| Laurylether sulfate, sodium salt ($C_{12}/C_{14}$ 70/30), oxyethylenated with 2.2 moles of ethylene oxide 28% in aqueous solution, sold by MARCHON under the trade name EMPICOL ESB/3 FL | 8.4 g AM |
| N-cocoamidoethyl-N-ethoxycarboxymethyl glycinate | 4 g AM |
| Hydroxyethylcellulose crosslinked with epichlorhydrine quaternized by trimethylamine, sold by NATIONAL STARCH under the trade name CELQUAT SC 240 | 0.35 g |
| Glycol distearate ($C_{16}/C_{18}$ 30/70) | 2 g |
| Coprah acid monoisopropanolamide | 3 g |
| Cross-linked polyacrylic acid sold by GOODRICH under the trade name CARBOPOL 980 | 0.2 g |
| Compound of Example I | 2 g |
| Preservatives, fragrance | |
| Water | qsp 100 g |

The pH was adjusted to 7.5 using sodium hydroxide.

EXAMPLE 8

Styling gel

| | |
|---|---|
| Cross-linked polyacrylic acid sold by GOODRICH under the trade name CARBOPOL 980 | 0.5 g |
| Vinlypyrrolidone/vinyl acetate copolymer (65/35), sold by BASF under the trade name LUVISCOL VA 64 | 2 g |
| Compound of Example I | 0.5 g |
| Water | qsp 100 g |

EXAMPLE 9

Perm lotion

A reducing permanent wave lotion for hair was prepared by mixing the following ingredients:

| | |
|---|---|
| Thioglycolic acid | 7 g |
| Glycerol thioglycolate, 68% AM in glycerol | 2 g AM |
| Oleic acid oxyethylenated with 20 moles of ethylene oxide, sold by ICI under the trade name BRIJ 98 | 2 g |
| Compound of Example I | 0.3 g |
| Monoethanolamine | qs pH = 7.5 |
| Demineralized water | qsp 100 g |

This composition was applied to wet hair which had been set onto rollers. After leaving the composition to act for a period of 15 minutes the hair was thoroughly rinsed with water and then the following oxidizing composition was applied:

| | |
|---|---|
| Hydrogen peroxide | qs 8 volumes |
| Oleic acid oxyethylenated with 20 moles of ethylene oxide, sold by ICI under the trade name BRIJ 98 | 1 g |
| Compound of Example I | 0.1 g |
| Phosphoric acid | qs pH = 3.0 |
| Demineralized water | qsp 100 g |

The oxidizing composition was allowed to act for about 5 minutes and then the rollers were removed and the hair was thoroughly rinsed with water. After drying under a hood the hair had beautiful curls.

EXAMPLE 10

A toothpaste was prepared by mixing the following compounds:

| | |
|---|---|
| Compound of Example I | 0.25 g |
| Amorphous precipitated silica sold by RHONE POULENC under the trade name TIXOSIL 73 | 12 g |
| Amorphous precipitated silica sold by RHONE POULENC under the trade name TIXOSIL 333 | 8 g |
| Sodium carboxymethylcellulose sold by HERCULES under the trade name BLANOSE 9M 31 F | 1.4 g |
| Sorbitol, 70% AM in aqueous solution | 22.4 g AM |
| Powdered lauryl sulfate, sodium salt, sold by MARCHON under the trade name EMPICOL LZV/E, 93% AM | 1.67 g AM |
| Sodium monofluorophosphate | 0.76 g |
| Titanium dioxide | 0.6 g |
| Methyl parahydroxybenzoate | 0.2 g |
| Sodium saccharinate | 0.15 g |
| Flavoring | qs |
| Water | qsp 100 g |

We claim:

1. A cosmetic treatment process, comprising applying to the body a cosmetic composition containing at least one compound with formula (I):

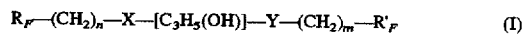

$$R_F\text{—}(CH_2)_n\text{—}X\text{—}[C_3H_5(OH)]\text{—}Y\text{—}(CH_2)_m\text{—}R'_F \qquad (I)$$

where
$C_3H_5$ (OH) represents the structures:

$$-CH_2-CH(OH)-CH_2- \quad (Ia)$$

$$-CH(CH_2OH)-CH_2- \quad (Ib)$$

$$-CH_2-CH(CH_2OH)- \quad (Ic)$$

$R_F$ and $R'_F$, which may be identical to or different from each other, represent a perfluorinated linear or branched $C_4$–$C_{20}$ alkyl radical;

m and n, which may be identical to or different from each other, are 0, 1, 2, 3 or 4;

X and Y, which may be identical to or different from each other, represent O or S.

2. Process according to claim 1, wherein in formula (I) $R_F$ and $R_{F'}$ represent a linear or branched perfluorinated $C_6$–$C_{10}$ alkyl radical;

X and Y are not both O;

n and m equal 2 and $$-C_3H_5(OH)- \text{ is } -CH_2-CH(OH)-CH_2-.$$

3. A cosmetic composition containing 0.1 to 25% by weight of at least one compound with formula (I):

$$R_F-(CH_2)_n-X-[C_3-H_5(OH)]-Y-(CH_2)_m-R'_F \quad (I)$$

where
$C_2H_5$(OH) represents the structures:

$$-CH_2-CH(OH)-CH_2- \quad (Ia)$$

$$-CH(CH_2OH)-CH_2- \quad (Ib)$$

$$-CH_2-CH(CH_2OH)- \quad (Ic)$$

$R_F$ and $R'_F$ which may be identical to or different from each other, represent a perfluorinated linear or branched $C_4$–$C_{20}$ alkyl radical;

m and n, which may be identical to or different from each other, are 0, 1, 2, 3 or 4;

X and Y, which may be identical to or different from each other, represent O or S, and a cosmetically effective amount of at least one cosmetic additive selected from the group consisting of fatty substances, organic solvents, silicones, thickeners, softeners, UV-A and UV-B and broad spectrum solar filters, anti-foaming agents, moisturizing agents, humectants, fragrances, preservatives, surfactants, fillers, sequestrating agents, emulsifiers, anionic, cationic, non-ionic and amphoteric polymers and mixtures thereof, antiperspirants, alkalinizing agents, dyes, pigments, propellants, reducing agents, anti-oxidizing agents and free radical absorbers.

4. A cosmetic composition according to claim 3 wherein it is in the form of a milk or cream, oily or oleoalcoholic lotion, oily or oleoalcoholic gel, ionic or non-ionic amphiphilic lipid based vesicular dispersion, solid stick, paste, spray or aerosol foam.

5. A cosmetic composition according to any one of claim 2, wherein it is in the form of a milk or cream for skin or hair, a make-up removing cream, lotion or milk, a sun protection cream, gel, milk or lotion, a shaving cream or foam, an aftershave lotion, a shampoo or conditioner, a body deodorant, a toothpaste, a lacquer, a lid, eyelash, nail, lip or skin make-up, a skin treatment cream, a foundation, a lipstick, an eyeshadow, a blusher, an eyeliner, a mascara, a lip care product or a nail care product.

6. A compound with formula (I'):

$$R_{F'}-(CH_2)_n-X-[C_3H_5(OH)]-Y-(CH_2)_m-R'_F \quad (I')$$

where
$C_3H_5$(OH) represents the structures:

$$-CH_2-CH(OH)-CH_2- \quad (Ia)$$

$$-CH(CH_2OH)-CH_2- \quad (Ib)$$

$$-CH_2-CH(CH_2OH)- \quad (Ic)$$

$R_F$ and $R_{F'}$, which may be identical to or different from each other, represent a perfluorinated linear or branched $C_4$–$C_{20}$ alkyl radical;

m and n, which may be identical to or different from each other, are 0, 1, 2, 3 or 4, and X represents O and Y represents S or X represents S and Y represents O.

7. A cosmetic composition according to claim 3 wherein in formula (I) $R_F$ and $R'_F$ represent a linear or branched perfluorinated $C_6$–$C_{10}$ alkyl radical;

X and Y are not both O;

n and m equal 2 and $-C_3H_5$(OH)— is $-CH_2-CHOH-CH_2-$.

* * * * *